United States Patent
LaVoie et al.

(10) Patent No.: US 9,562,051 B2
(45) Date of Patent: Feb. 7, 2017

(54) METHYLENEDIOXYBENZO [I] PHENANTHRIDINE DERIVATIVES USED TO TREAT CANCER

(75) Inventors: Edmond J. LaVoie, New Brunswick, NJ (US); Wei Feng, New Brunswick, NJ (US); Leroy F. Liu, Somerset, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/255,081

(22) PCT Filed: Mar. 5, 2010

(86) PCT No.: PCT/US2010/026381
§ 371 (c)(1),
(2), (4) Date: Sep. 6, 2011

(87) PCT Pub. No.: WO2010/102219
PCT Pub. Date: Sep. 10, 2010

(65) Prior Publication Data
US 2012/0101117 A1    Apr. 26, 2012

Related U.S. Application Data

(60) Provisional application No. 61/158,156, filed on Mar. 6, 2009.

(51) Int. Cl.
*C07D 491/04* (2006.01)
*A61K 31/4355* (2006.01)

(52) U.S. Cl.
CPC ......... *C07D 491/04* (2013.01); *A61K 31/4355* (2013.01)

(58) Field of Classification Search
None
See application file for complete search history.

(56) References Cited

U.S. PATENT DOCUMENTS

| | | |
|---|---|---|
| 2,915,523 A | 12/1959 | Moore et al. |
| 2,981,731 A | 4/1961 | Moore et al. |
| 2,985,661 A | 5/1961 | Hien et al. |
| 3,267,107 A | 8/1966 | Sallay |
| 3,272,707 A | 9/1966 | Tedeschi |
| 3,449,330 A | 6/1969 | Guglielmetti et al. |
| 3,538,097 A | 11/1970 | Lowe et al. |
| 3,542,782 A | 11/1970 | Houlihan et al. |
| 3,849,561 A | 11/1974 | Junzo et al. |
| 3,884,911 A | 5/1975 | Shimada et al. |
| 3,912,740 A | 10/1975 | Zee-Chang et al. |
| 4,749,708 A | 6/1988 | Maroko |
| 4,761,417 A | 8/1988 | Maroko et al. |
| 4,761,477 A | 8/1988 | Ikekawa et al. |
| 4,925,943 A | 5/1990 | Kanmacher et al. |
| 4,980,344 A | 12/1990 | Maroko |
| 5,106,863 A | 4/1992 | Hajos et al. |
| 5,126,351 A | 6/1992 | Luzzio et al. |
| 5,153,178 A | 10/1992 | Maroko |
| 5,190,753 A | 3/1993 | Behrens et al. |
| 5,244,903 A | 9/1993 | Wall et al. |
| 5,318,976 A | 6/1994 | Luzzi et al. |
| 5,639,759 A | 6/1997 | Magolda et al. |
| 5,646,283 A | 7/1997 | Suzuki et al. |
| 5,767,142 A | 6/1998 | LaVoie et al. |
| 5,770,617 A | 6/1998 | LaVoie et al. |
| 5,807,874 A | 9/1998 | LaVoie et al. |
| 5,981,541 A | 11/1999 | LaVoie et al. |
| 6,140,328 A | 10/2000 | LaVoie et al. |
| 6,509,344 B1 | 1/2003 | Cushman et al. |
| 6,740,650 B2 | 5/2004 | LaVoie et al. |

(Continued)

FOREIGN PATENT DOCUMENTS

| | | |
|---|---|---|
| EP | 0108147 B1 | 5/1984 |
| EP | 0496634 A1 | 7/1992 |

(Continued)

OTHER PUBLICATIONS

Aguirre, J. M. et al., "Reaction of 1,2-diarylethylamides with ethyl polyphosphate(EPP): correlation of the von Braun, Ritter and Bischler-Napieralski reactions." Chemical Abstracts, 111(13), Abstract No. 115004, 656 (1989).

Akiyama et al., "Isolation and Genetic Characterization of Human KB Cell Lines Resistant to Multiple Drugs", *Somatic Cell and Molecular Genetics*, vol. 11, No. 2, 117-126 (1985).

Andoh et al., "Characterization of a mammalian mutant with a camptothecin-resistant DNA topoisomerase I", *Proc. Natl. Acad. Sci.*, vol. 84, 5565-5569 (1987).

(Continued)

*Primary Examiner* — Jeffrey S Lundgren
*Assistant Examiner* — Stephanie Springer
(74) *Attorney, Agent, or Firm* — Viksnins Harris & Padys PLLP

(57) ABSTRACT

The invention provides compounds of formula I: wherein A, B, X, and Y have any of the values defined in the specification, as well as pharmaceutical compositions comprising such compounds, processes for preparing such compounds, and therapeutic methods for treating cancer and other topoisomerase mediated conditions.

(I)

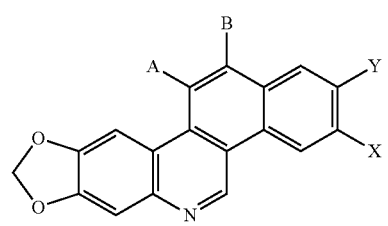

17 Claims, No Drawings

(56) References Cited

U.S. PATENT DOCUMENTS

| | | | |
|---|---|---|---|
| 7,208,492 B2* | 4/2007 | LaVoie et al. | 514/248 |
| 7,517,867 B2 | 4/2009 | LaVoie et al. | |
| 7,858,627 B2 | 12/2010 | LaVoie et al. | |
| 2005/0009825 A1 | 1/2005 | LaVoie et al. | |
| 2005/0009826 A1 | 1/2005 | LaVoie et al. | |
| 2005/0010046 A1 | 1/2005 | LaVoie et al. | |
| 2012/0004235 A1* | 1/2012 | Lavoie et al. | 514/248 |

FOREIGN PATENT DOCUMENTS

| | | |
|---|---|---|
| GB | 2108955 A | 5/1983 |
| SU | 1530628 A1 | 12/1989 |
| WO | WO 92/21661 A1 | 12/1992 |
| WO | WO 96/36612 A1 | 11/1996 |
| WO | WO 97/29106 A1 | 8/1997 |
| WO | WO 98/12181 A1 | 3/1998 |
| WO | WO 98/31673 A1 | 7/1998 |
| WO | WO 99/31067 A1 | 6/1999 |
| WO | WO 00/21537 A1 | 4/2000 |
| WO | WO 01/32631 A2 | 5/2001 |
| WO | WO 03/41660 A2 | 5/2003 |
| WO | WO 03/047505 A2 | 6/2003 |
| WO | WO 2004/014918 A1 | 2/2004 |
| WO | WO 2004/044174 A2 | 5/2004 |

OTHER PUBLICATIONS

Andoh et al., "Drug Resistance Mechanisms of Topoisomerase / Drugs", *Advances in Pharmacology*, vol. 29B, DNA Topoisomerases: Topoisomerase-Targeting Drugs, 93-103 (1994).
Arumugam et al., "Synthesis of 7, 8-Benzophenanthridines" *Indian Journal of Chemistry*, vol. 12, 664-667 (1974).
Badia et al., "Silicon-mediated isoquinoline synthesis: preparation and stereochemical characterization of 4-hydroxy-3-phenylisoquinolines", *Chemical Abstracts*, vol. 117 (13), Abstract No. 131034, 730 (1992).
Baezner, Conversion of o-nitrobenzyl chloride and o,p-dinitrobenzyl chloride into acridine derivatives, 3077-3083 (1904) [with English Abstract].
Baezner et al., Conversion of o-nitro and o,p-dinitrobenzylchloride into acridinic derivatives, 2438-2447 (1906) [with English Abstract].
Bhakuni, D.S. et al., "Protoberberine Alkaloids", *The Alkaloids*, vol. 28, Chapter 2, Academic Press, Inc., 95-181 (1986).
Bjornsit, M-A. et al., "Expression of human DNA topoisomerase I in yeast cells lacking yeast DNA topoisomerase I: restoration of sensitivity of the cells to the antitumor drug camptothecin", *Cancer Research*, 49, 6318-6323 (1989).
Bradsher, C.K. et al., "Alpha-Acyl-o-tolunitriles as intermediates in the preparation of 3-substituted isoquinolines and 1-amino-2-benzopyrylium derivatives", *Chemical Abstracts*, 89(21), Abstract No. 89: 179810b, 590 (1978).
Brossi, A., "Benzo[c]phenanthridine Alkaloids", *The Alkaloids, Chemistry and Pharmacology*, vol. XXV, Academic Press, Inc., 178-199 (1985).
Buu-Hoi, N.P. et al., "Carcinogenic Nitrogen Compounds. XV. Polysubstituted Angular Benacridines and Benzophenarsazines", *Chemical Abstracts*, 49(1), Abstract, col. 330, 10—Organic Chemistry, 329-330 (1955).
Buu-Hoi, N.G. et al., "The Chemistry of Carcinogenic Nitrogen Compounds. Part X. The Pfitzinger Reaction in the Synthesis of 1:2-Benzacridines", *Journal of the Chemical Society*, Letchworth, GB, 279-281 (1952).
Buu-Hoi, N.G., "The chemistry of carcinogenic nitrogen compounds. Part V. Angular hydroxybenzacridines and hydroxdibenzacridines", *Journal of the Chemical Society*, Letchworth GB, (1950), 2096-2099 (1950).
Carmichael, J., "Evaluation of a tetrazolium-based semiautomated colorimetric assay: assessment of chemosensitivity testing", *Cancer Research*, 47, 936-42 (1987).

Chen, A.Y., "A new mammalian DNA topoisomerase I poison Hoechst 33342: cytotoxicity and drug resistance in human cell cultures", *Cancer Research*, 53(6), 1332-1337 (1993).
Chen, et al., "DNA Minor Groove-Binding Ligands: A Different Class of Mammalian DNA Topoisomerase I Inhibitors", *Proceedings of the National Academy of Sciences*, 90, 8131-8135 (1993).
Chen, et al., "DNA Topoisomerases: Essential Enzymes and Lethal Targets", *Annu. Rev. Pharmacol. Toxicol.*, 34, 191-218 (1994).
Cherif, A. et al., "N-(5,5-Diacetoxypent-1-yl)doxorubicin: a new intensely potent doxorubicin analogue", *Journal of Medicinal Chemistry*, 35, 3208-3214 (1992).
Croisy-Delcey, M. et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", *Chemical Abstracts*, 98, Abstract No. 43798, 27-29 (1983).
Croisy-Delcey, M. et al., "Synthesis and carcinogenic activity of oxidized benzacridines: potential metabolites of the strong carcinogenic 7-methylbenz[c]acridine and of the inactive isomer 12-methylbenz[a]acridine." *Journal of Medicinal Chemistry*, 26, 303-306 (Abstract) (1983).
Cushman, M. et al., "Synthesis and antitumor activity of structural analogues of the anticancer benzophenanthridine alkaloid fagaronine chloride", *Journal of Medicinal Chemistry*, 28, 1031-1036 (1985).
Cushman, et al., "Synthesis of New Indeno[1,2-c]isoquinolines: Cytotoxic Non-Camptothecin Topoisomerase I Inhibitors", *Journal of Medicinal Chemistry*, 43(20), 3688-3698 (2000).
D'Arpa, et al., "Topoisomerase-targeting antitumor drugs", *Biochimica et Biophysica Acta*, 989, 163-177 (1989).
Denizot, F. et al., "Rapid colorimetric assay for cell growth and survival. Modifications to the tetrazolium dye procedure giving improved sensitivity and reliability", *Journal of Immunological Methods*, 89, 271-277 (1986).
Denny, "Emerging DNA topoisomerase inhibitors as anticancer drugs", *Expert Opin. Emerg. Drugs*, vol. 9(1), 105-133 (2004).
Dominguez, E. et al., "Dehydrogenation reactions of 1-substituted-3-aryltetrahydro-isoquinoline derivatives", *Chemical Abstracts*, 101(11), Abstract No. 090742z,(1984).
Dorofeenko, G. N. et al., "Synthesis of 3-aryl derivatives of 2-benzopyrylium salts with free alpha-positions", (1971). *Chemical Abstracts*, 74 (15), Abstract No. 076295, 432 (1971).
Feng et al., "11-Substituted 2,3-dimethoxy-8,9-methylenedioxybezo[i]phenanthridine derivatives as novel topoisomerase I-targeting agents", Bioorganic & Medicinal Chemistry 16, 8598-8606 (2008).
Fitzgerald, J. J. et al., "Reaction of benzocyclobutene oxides with nitriles: synthesis of hypecumine and other 3-substituted isoquinolines", *Chemical Abstracts*, 122(7), Abstract No. 081704, 1128 (1995).
Fox, G.J. et al., "para-Bromination of Aromatic Amines: 4-Bromo-N,N-Dimethyl-3-(Trifluoromethyl)Aniline", *Organic Syntheses*, vol. 55, 20-23 (1976).
Fuji, N. et al., "Induction of Mammalian DNA Topoisomerase I-mediated DNA Cleavabe and DNA Winding by Bulgarein", *Journal of Biological Chemistry*, 268(18), 13160-13165 (1993).
Gallo, R.C. et al., "Studies on the Antitumor Activity, Mechanism of Action, and Cell Cycle Effects of Camptothecin", *Journal of the National Cancer Institute*, vol. 46, No. 4, 789-795 (1971).
Garcia, A. et al., "A simple direct approach to 1-substituted 3-arylisoquinolines from deoxybenzoins and nitriles", *Chemical Abstracts*, 110(25), Abstract No. 23107u, 622 (1989).
Gatto, B., "Identification of Topoisomerase I as the Cyctotoxic Target of the Protoberberine Alkaloid Coralyne", *Cancer Research*, 56(12), 2795-2800 (1996).
Giovanella, B.C. et al., "Complete growth inhibition of human cancer xenografts in nude mice by treatment with 20-(S)-camptothecin", *Cancer Research*, 51(11), 3052-3055 (1991).
Godowski, K.C. et al., "Free amine benzophenanthridine alkaloid compositions", USPATFULL Database, No. 95:20510, RN No. 218-38-2 (Benzo[c]phenanthradine), from U.S. Pat. No. 5,395,615, (1995), 3 pages.

(56) References Cited

OTHER PUBLICATIONS

Goldman, G.H. et al., "Differential poisoning of human and Aspergillus nidulans DNA topoisomerase I by bi- and terbenzimidazoles", *Biochemistry*, 36(21), (1997), 6488-6494 (1997).

Gopinath, K.W. et al., "Synthesis of Some 1:2- and 7:8-Benzophenanthridine", *Journal of the Chemistry Society*, 78(2), 504-509 (1958).

Hahn, F.E. et al., "Berberine", *Antibiotics, Mechanism of Action of Antimicrobial and Antitumor Agents*, vol. III, J.W. Corcoran et al., (eds.), Springer-Verlag, 577-584 (1975).

Halligan, B.D. et al., "Purification and Characterization of a Type II DNA Topoisomerase from Bovine Calf Thymus", *The Journal of Biological Chemistry*, 260(4), 2475-2482 (1985).

Hoan, N. et al., "Syntheses from o-halogenated anisoles and phenetoles", *Chemical Abstracts*, 41(20), American Chemical Society, Abstract No. 6571bg, 2 pages (1947).

Hsaing et al., "Camptothecin Induced Protein-Linked DNA Breaks Via Mammalian DNA Topoisomerase I", *J. Biol. Chem.*, 260 No. 27, 14873-14878 (1985).

Hsiang, Y-H et al., "Identification of Mammalian DNA Topoisomerase I as an Intracellular Target of the Anticancer Drug Camptothecin", *Cancer Research*, 48(7), 1722-1726 (1988).

Iwao, M. et al., "A Regiospecific Synthesis of Carbazoles via Consecutive Palladium-Catalyzed Cross-coupling and Aryne-Mediated Cyclization", *Heterocycles*, 36, 1483-1488 (1993).

Izmail'skii, V. A. et al., "Absorption Spectra of Molecular Complexes of Derivatives of Benzacridine and Dibenzacridine", Chemical Abstracts, 54(8), Abstract, col. 7335b, 3 pages (1960).

Jacob, J. et al., "Monooxygenase Induction by Various Xenobiotics and its Influence on Rat Liver Microsomal Metabolism by Chrysene in Comparison to Benz[a]anthracene", *Chemical Abstracts*, 107, Abstract No. 34760, 2 pages (1987).

Janin, Y.L. et al., "Synthesis and Evaluation of New 6-Amino-Substituted Benzo[c]phenanthridine Derivatives", *Journal of Medicinal Chemistry*, 36(23), 3686-3692 (1993).

Jayaraman, M. et al., "Synthesis of New Dihydroindeno [1,2-c] isoquinoline and Indenoisoquinolinium Chloride Topoisomerase Inhibitors Having High in Vivo Anticancer Activity in the Hollow Fiber Animal Model", *Journal of Medicinal Chemistry*, 45(1), 242-249 (2002).

Kametani, Tetsuji et al., "Studies on the synthesis of heterocyclic compounds. DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", *Chemical and Pharmaceutical Bulletin*, 23(9), 2025-2028 (1975).

Kametani, T. et al., "Synthesis of Heterocyclic Compounds. DCXXVII. Formation of 2,3,9,10-tetramethoxybenz[c]acridine by treatment of 6,7-dimethoxy-1-(4,5-dimethoxy-2-nitrophenethyl)-2-methylisoquinoline with Triethyl Phosphite", *Chemical Abstracts*, 84, Abstract No. 43798, 1 page (1976).

Kanmacher, I. et al., "Synthesis of Isoquino[1,2-b]quinazolines by Cycloaddition Reaction", *Chemical Abstracts*, 114, Abstract No. 207191, 4 pages (1990).

Kar, G.K. et al., "Regioselective Thermal Cyclization of 3-substituted Arylenaminoimine hydrochlorides. A convenient method for the synthesis of Functionalized Polycyclic Quinoline Derivatives", *Chemical Abstracts*, 123, Abstract No. 11828, 1 page (1995).

Kerrigan, J.E. et al., "5H-8,9-Dimethoxy-5-(2-N,N-dimethylaminoethyl)dibenzo[c,h][1,6]naphthyridin-6-ones and Related Compounds as TOP1-Targeting Agents: Influence of Structure on the Ternary Cleavable Complex Formation", *Bioorganic and Medicinal Chemistry Letters*, 13, 3395-3399 (2003).

Kessar, SV. et al., "Azasteroids. Part VII. Synthesis of 7-hydroxy-2-methoxy-7,8,9,10-tetrahydrobenzo[i]phenanthridine", *J. Chem. Soc.*, 259-261 (1971).

Kessar, S.V. et al., "New Routes to Condensed Polynuclear Compounds: Part X-Synthesis of Some Benzo[i]phenanthridine through Benzyne Cyclization", *Indian Journal of Chemistry*, 11, 624-627 (1973).

Kim, J.S. et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada, 451 (Mar. 1995).

Kim, J.S. et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey*, Princeton, Marriott Forrestal Village, 28 (1995).

Kim, J.S. et al., "Steric factors associated with the topoisomerase I inhibition and cytotoxicity of substituted bisbenzimidazoles", *Abstract 10—Proceedings of the American Association of Pharmaceutical Scientists Eastern Regional Meeting*, 27 (1995).

Kim, J.S. et al., "Structure-activity Relationships of Benzimidazoles and Related Heterocycles as Topoisomerase I Poisons", *Bioorganic & Med. Chem.*, 4, 621-630 (1996).

Kim, J.S., "Substituted 2,5'-Bi-1H-benzimidazoles: Topoisomerase I Inhibition and Cytotoxicity", *Journal of Medicinal Chemistry*, 39(4), 992-998 (1996).

Kim, J. S. et al., "Terbenzimidazoles: influence of 2"-, 4-, and 5-substituents on cytotoxicity and relative potency as topoisomerase I poisons", *Journal of Medicinal Chemistry*, 40(18), 2818-2824 (1997).

Kim, J.S. et al., "Quantitative structure-activity relationships on 5-substituted terbenzimidazoles as topoisomerase I poisons and antitumor agents", *Bioorganic & Medicinal Chemistry*, 6(2), 4 pages [Abstract] (1998).

Kitamura, T. et al., "Isoquinoline derivatives from the Ritter-type reaction of vinyl cations", *Chemical Abstracts*, 102(1), Abstract No. 6157c, (1985).

Klopman, G. et al., "Testing by Artificial Intelligence: Computational Alternatives to the Determination of Mutagenicity", *Chemical Abstracts*, 118, Abstract No. 17489, 1 page (1993).

Knab, A.M. et al., "Mechanisms of Camptothecin Resistance in Yeast DNA Topoisomerase I Mutants", *Journal of Biological Chemistry*, 268(30), 22322-22330 (1993).

LaVoie, E.J. et al., "Structure-activity studies related to minor groove-binding ligands which inhibit mammalian DNA topoisomerase I", Abstract 1—Proceedings of the 85th Annual Meeting of American Association for Cancer Research, San Francisco, CA, 2699 (Apr. 1994).

Lee, J. S. et al., "Coralyne binds tightly to both T A T- and C G C+-containing DNA triplexes", *Biochemistry*, 32(21), 5591-5597 (1993).

Liu, L.F. et al., "Cleavage of DNA by Mammalian DNA Topoisomerase II", *Journal of Biological Chemistry*, vol. 258, No. 24, 15365-15370 (1983).

Makhey, D., "Protoberberine Alkaloids and Related Compounds as Dual Inhibitors of Mammalian Topoisomerase I and II", *Medicinal Chemistry Research*, 5(1), 1-12 (1994).

Makhey, D., "Coralyne and Related Compounds as Mammalian Topoisomerase I and Topoisomerase II Poisons", *Bioorganic & Medicinal Chemistry*, 4(6), 781-791 (1996).

Meegalla, S.K. et al., "Synthesis and Pharmacological Evaluation of Isoindolo[1,2-b]quinazolinone and Isoindolo[2,1-a]benzimidazole Derivatives Related to the Antitumor Agent Batracylin", *J. Med. Chem.*, 37, 3434-3439 (1994).

Memetzidis, G. et al., "Structure-affinity relationships of berbines or 5,6,13,13a-tetrahydro-8H-dibenzo[a,g]quinolizines at alpha-adrenoceptors", *European Journal of Medicinal Chemistry*, 26, 605-611 (1991).

Messmer, F.M. et al., "Fagaronine, a New Tumor Inhibitor Isolated from Fagara zanthoxyloides Lam. (Rutaceae)", *Journal of Pharmaceutical Sciences*, 1858-1859 (1972).

Mohanty, N. et al., "New Therapeutic agents of the quinoline series. I. Fused quinolyl compounds", *Chemical Abstracts*, XP 002049521, 1792 (1968).

(56) References Cited

OTHER PUBLICATIONS

Mosmann, "Rapid Colorimetric Assay for Cellular Growth and Survival: Application to Proliferation and Cytotoxicity Assays", *Journal of Immunological Methods*, 65(1-2), 55-63 (1983).
Nelson, J.T. et al., "Proton and carbon-13 NMR spectra of fifteen substituted isoquinolines", *Chemical Abstract*, 115(5), Abstract No. 048721, 753 (1991).
Patent Cooperation Treaty, International Searching Authority, Search Report and Written Opinion for PCT/US2010/026381, 15 pages, May 26, 2010.
Peters, D. et al., "Synthesis of Various 5-Substituted Uracils", *Journal of Heterocyclic Chemistry*, 27, 2165-2173 (1990).
Pilch, D. S. et al., "Biophysical Characterization of a Cytotoxic, Topoisomerase I Poison", *Abstract 8—Proceedings of the 3rd Annual Scientific Retreat of the Cancer Institute of New Jersey, Princeton Marriott Forrestal Village, Princeton, NJ*, 2 pages (Jun. 1, 1995).
Pilch, D.S. et al., "Characterizing the DNA binding modes of a topoisomerase I-poisoning terbenzimidazole: evidence for both intercalative and minor groove binding properties", *Drug Design and Discovery*, 13, 115-133 (1996).
Pilch, D.S. et al., "A terbenzimidazole that preferentially binds and conformationally alters structurally distinct DNA duplex domains: a potential mechanism for topoisomerase I poisoning", *Proc. Nat'l. Acad. Sci. USA*, 94(25), 13565-13570 (1997).
Piper, J.R. et al., "Synthesis and Antifolate Activity of 5-Methyl-5,10-dideaza Analogues of Aminopterin and Folic Acid and an Alternative Synthesis of 5, 10-Dideazatetrahydrofolic Acid, a Potent Inhibitor of Glycinamide Ribonucleotide Formyltransferase", *J. Med. Chem.*, 31, 2164-2169 (1988).
Porai-Koshits, B.A. et al., "Imidazole derivatives. IV. Synthesis of some polybenzimidazoles", J. Gen. Chem. USSR, 23, As related in Chemical Abstracts, 48(10) (1954), col. 12740, (1953), pp. 873-879 (1953).
Quast, U. et al., "Heterocyclic alpha-carbinolamines with the isoquinuclidines skeleton. 3. Benzoisoquinuclidines", *Chemical Abstracts*, 97 (21), Abstract No. 182180s, 806 (1982).
Ramesh, D. et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts*, 108, Abstract No. 37626, 2 pages (1988).
Ray, J.K. et al., "A Facile and Convenient Method for the Synthesis of 8-methoxy-10,11-dihydronaphtho[1,2-b]quinolones", *Chemical Abstracts*, 92, Abstract No. 76254, 30-31 (1980).
Ruchelman et al., "Dimethoxybenzol[i]phenanthridine-12-carboxylic acids derivatives and 6H-dibenzol[c,h][2,6]naphthyridin-5-ones with potent topoisomerase I-targeting activity and cytotoxicity", *Bioorganic & Medicinal Chemistry Letters*, 14, 5585-5589 (2004).
Safaryan, G.P. et al. "2-Benzopyrylium salts. 25, Reaction of 2-benzopyrylium salts with some nucleophiles", *Chemical Abstracts*, 96(17), Abstract No. 142656z, 739 (1982).
Schiess, P. et al., "Thermolytic ring opening of acyloxybenzocyclobutenes: an efficient route to 3-substituted isoquinolines", *Chemical Abstracts*, 104(19), Abstract No. 168332z, 639 (1986).
Sethi, M.L., "Enzyme Inhibition VI: Inhibition of Reverse Transcriptase Activity by Protoberberine Alkaloids and Structure-Activity Relationships", *Journal of Pharmaceutical Sciences*, 72(5), 538-541 (1983).
Shcherbakova, I.V. et al., "2-Benzopyrilium salts. 35. Synthesis of the natural alkaloid dehydronocoralydine and other substituted salts of dibenzo[a,g] quinolizine", *Chemical Abstracts*, 112 (19), Abstract No. 179554, 823 (1990).
Singh, M.P. et al., "Synthesis and Sequence-Specific DNA Binding of a Topoisomerase Inhibitory Analog of Hoechst 33258 Designed for Altered Base and Sequence Recognition", *Chem. Res. Toxicol.*, 5, 597-607 (1992).
Singh, S.K. et al., "Nitro and Amino Substitution in the D-Ring of 5-(2-Dimethylaminoethyl)-2,3-methylenedioxy-5H-dibenzo [c,h] [1,6] naphthyridin-6-ones: Effect on Topoisomerase-I Targeting Activity and Cytotoxicity", *Journal of Medicinal Chemistry*,46(11), 2254-2257 (2003).
Sotomayor, N. et al., "Oxidation reactions of 2'-functionalized 3-aryltetrahydro- and 3,4-dihydroisoquinolines", *Chemical Abstracts*, 124 (11), Abstract No. 145854, 1227 (1996).
Southard, G.L. et al., "Drug Delivery Devices", USPATFULL Database, No. 91:36238, RN No. 215-38-2 (Benzo[c]phenanthradine), from U.S. Pat. No. 5,013,553, 2 pages (1991).
Stermitz, F.R., "Synthesis and Biological Activity of Some Antitumor Benzophenanthridinum Salts", *Journal of Medicinal Chemistry*, 18(7), 708-713 (1975).
Studier, F.W. et al., "Use of T7 RNA polymerase to direct expression of cloned genes", *Methods in Enzymology*, 185, 60-89 (1990).
Sun, Q. et al., "Structure-activity studies related to minor groove-binding ligands which inhibit mammalian DNA topoisomerase I", *Cancer Institute of New Jersey's First Annual Scientific Retreat, Abstract 2, Princeton Marriott Forrestal Village, Princeton, NJ*, p. 66 (Jun. 7, 1994).
Sun, Q. et al., "Structure Activity of Topoisomerase I Poisons Related to Hoechst 33342", *Bioorganic & Medicinal Chemistry Letters*, 4 (24), 2871-2876 (1994).
Sun, Q. et al., "Structure activity of novel topoisomerase I inhibitors related to Hoechst 33342", *Abstract 6—Proceedings of the American Association of Pharmaceutical Scientists Eastern Regional Meeting, Hyatt Regency Hotel, New Brunswick, NJ*, p. 25 (Jun. 5-6, 1995).
Sun, Q. et al., "Synthesis and evaluation of terbenzimidazoles as topoisomerase I inhibitors", *Journal of Medicinal Chemistry*, 38(18), 3638-3644 (1995).
Sun, Q. et al., "Synthesis and Evaluation of Terbenzimidazoles as Topoisomerase I Inhibitors", *Chemical Abstracts*, vol. 123, No. 15, Abstract No. 198740r, 1241 (1995).
Sun, Q. et al., "Synthesis and Pharmacological Evaluation of a Series of Novel DNA Topoisomerase I Inhibitors as Antitumore Agents", *Scientific Proceedings of 86th Annual Meeting of the American Association Cancer Research, Abstract 3, vol. 36, Toronto, Canada*, 2688 (Mar. 1995).
Sun, Q. et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey, Princeton Marriott Forrestal Village, Princeton, NJ*, p. 27 (1995).
Sun, Q. et al., "Synthesis of Benzimidazo[2,1-a]isoquinolines", *Syn. Lett.*, submitted, Paper No. 7, 6 pages (1995).
Tamura, H. et al., "Molecular cloning of a cDNA Dna topoisomerase I and identification of mutation a), 69-75 (1991). of a camptothecin-resistant human sites", Nucleic Acids Research, 19.
Tewey, Km. et al., "Adriamycin-induced Dna damage mediated by mammalian Dna topoisomerase Ii", *Science*, 226(4673), 466-8 (1984).
Vinogradov, a.E. et fluorochromes without a 270 (1993). al., "Some properties of new Dna specific bisbenzimidazole piperazine ring", Biotechnic & Histochemistry, 68 (5), 265-.
Walterova, D. et al., "Isolation, Chemistry and Biology of Alkaloids from plants of Papaveraceae. Part Xcv. Practical application of isotachophoresis in analysis of isoquinoline alkaloids", Chemical Abstract, vol. 104, No. 12, No. 95573, (1986).
Wang, L.k. et al., "Inhibition of Topoisomerase I Function by Nitidine and Fagaronine", *Chem. Res. Toxicol.*, 6, 813-818 (1993).
Wang, L-K et al., "Inhibition of Topoisomerase I Function by Coralyne and 5,6- Dihydrocoralyne", *Chem. Res. Toxicol.*, 9, 75-83 (1996).
Wang, H. et al., "Stimulation of topoisomerase Ii-mediated Dna damage via a mechanism involving protein thiolation", Biochemistry, 40(11), 3316-3323 (2001).
Waters, W.A. et al., "Reactions of Free Benzyl Radicals with Benz[a]- and Benz[c]acridine", *Chemical Abstracts*, 54 (4), Abstract, Col. 3424b, (1960).
Wilson, W.D. et al., "Coralyne. Intercalation with Dna as a Possible Mechanism of Antileukemic Action", Journal of Medicinal Chemistry, 19(10), Communications to.The Editor, 1261-1263 (1976).

(56) References Cited

OTHER PUBLICATIONS

Yadagiri, B. et al., "Convenient Routes to Substituted Benzimidazoles and Imidazolo[4,5-b]pyridines Using Nitrobenzene as Oxidant", *Synthetic Communications*, 20 (7), 955-963 (1990).

Yamamoto, Y et al., "Reaction of 6H-1, 3-oxazin-6-one with benzyne giving isoquinoline derivatives", *Chemical Abstracts*, 118(7), Abstract No. 059563u, 831 (1993).

Yamashita, Y. et al., "Induction of Mammalian DNA Topoisomerase I and Ii Mediated DNA Cleavage by Saintopin, a New Antitumor Agent from Fungus", *Biochemistry*, 30(24), 5838-5845 (1991).

Yamashita, Y., "Induction of Mammalian DNA Topoisomerase I Mediated DNA Cleavage by Antitumor Indolocarbazole Derivatives", 12075 (1992) *Biochemistry*, 31(48), 12069-12075 (1992).

Zee-Cheng, K.Y. et al., "Practical Preparation of Coralyne Chloride", *Journal of Pharmaceutical Sciences*, 61 (b), 969-971 (1972).

Zee-Cheng, K. et al., "Experimental Antileukemic Agents. Coralyne, Analogs, and Related Compounds", *Journal of Medicinal Chemistry*, 17(3), 347-351 (1974).

Zee-Cheng, R.K. et al., "Tetramethoxydibenzoquinolizinium Salts. Preparation and Antileukemic Activity of Some Positional and Structural Isomers of Coralyne", *Journal of Medicinal Chemistry*, 19(7), 882-886 (1976).

Zhu et al., "Esters and amides of 2,3-dimethoxy-8,9-methylenedioxy-benzo[i]phenanthridine-12-carboxylic acid: Potent cytotoxic and topoisomerase I-targeting agents", *Bioorganic & Medicinal Chemistry*, 13, 6782-6794 (2005).

\* cited by examiner

METHYLENEDIOXYBENZO [I] PHENANTHRIDINE DERIVATIVES USED TO TREAT CANCER

CROSS-REFERENCE TO RELATED APPLICATION

This application claims priority to U.S. Provisional Application No. 61/158,156, filed on Mar. 6, 2009 the specification of which is herein incorporated by reference.

GOVERNMENT FUNDING

The invention described herein was made with government support under Grant Numbers CA098127, CA39662, and CA077433 awarded by the National Cancer Institute. The United States Government has certain rights in the invention.

BACKGROUND OF THE INVENTION

Topoisomerases are ubiquitous enzymes that participate in processes such as DNA replication, repair, transcription, and recombination as well as chromosome condensation and segregation. Topoisomerase I (TOP1) is the target of several antitumor agents based upon their ability to stabilize the enzyme-DNA cleavage complex, which results in DNA damage and ultimately cell death. Camptothecin (CPT) was the first compound identified as a TOP1-targeting agent (Hsaing, Y. H.; Hertsberg, R.; Hecht, S.; Liu, L. F. Camptothecin Induced Protein-Linked DNA Breaks Via Mammalian DNA Topoisomerase I, *J. Biol. Chem.*, 1985, 260, 14873-14878). Two clinical TOP1-targeting agents, topotecan (Hycamtin®) and irinotecan (CPT-11/Camptosar®) have since been developed. The improved water-solubility of topotecan and irinotecan relative to CPT was critical to their development into the clinic. These agents have incorporated, within their structure, the core structure of camptothecin, which includes a δ-lactone. This lactone moiety is susceptible to hydrolysis and the resulting carboxylic acid has a high affinity for human serum albumin. In addition, it is known that both of these clinical agents are susceptible to transporter-mediated cellular efflux, which can limit intracellular accumulation and has been associated with multidrug resistance. Specifically overexpression of MDR1 (P-glycoprotein) and breast cancer resistance protein (BCRP) have been associated with resistance to these camptothecins.

Additional topoisomerase targeting agents with anticancer properties include those described by LaVoie et al. in U.S. Pat. No. 7,208,492. Particular compounds discussed include compound 206 and compound 216.

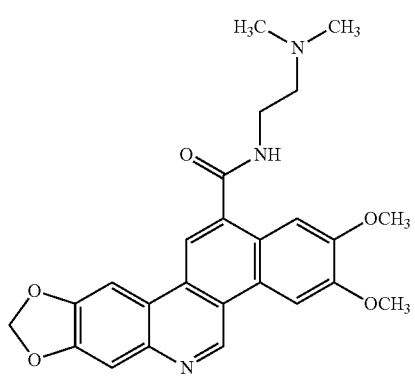

206

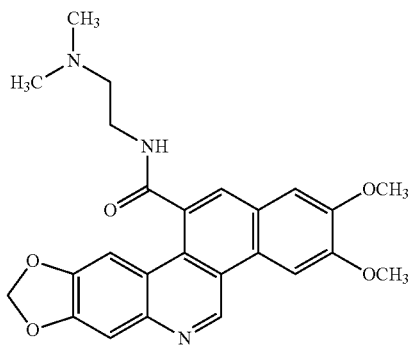

216

These are the compounds of formula II and formula I respectfully, as described in U.S. Pat. No. 7,208,492.

Despite these previous reports there is currently a need for additional agents that are useful for treating cancer. There is also a need for anticancer agents, particularly topoisomerase I targeting agents that have enhanced cytotoxicity or enhanced metabolic stability, prolonged half-lives or improved oral bioavailability in mammals, or for topoisomerase I targeting agents that are not substrates for an efflux transporter or that have a diminished ability to be removed from a cell by an efflux transporter.

SUMMARY OF THE INVENTION

The present invention provides compounds that show inhibitory activity against topoisomerase I and/or topoisomerase II and compounds that are effective cytotoxic agents against cancer cells including drug-resistant cancer cells. The compounds of the invention are based on a benzo[i]phenanthridine core with a carboxamide moiety comprising an alkyl group with a pendant amino group for which the methylene adjacent to the amino group is disubstituted. Applicant has discovered that disubstitution of this methylene adjacent to the amino group provides compounds with significantly enhanced cytotoxicity relative to the compounds for which the methylene is unsubstituted. Representative compounds of the invention were found not to be substrates of BCRP.

Accordingly there is provided a compound of the invention which is a compound of formula I:

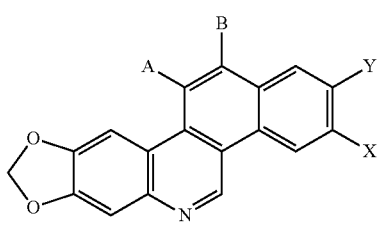

I wherein:
one of A and B is —C(O)NH(CR$^6$R$^7$)$_n$CR$^1$R$^2$NR$^a$R$^b$ and the other is H;

R$^1$ and R$^2$ are each independently (C$_1$-C$_3$) alkyl; or R$^1$ and R$^2$ together with the carbon to which they are attached form a 3-6 membered cycloalkyl;

R$^a$ and R$^b$ are each independently H or (C$_1$-C$_3$) alkyl wherein (C$_1$-C$_3$) alkyl may be optionally substituted with aryl or heteroaryl; or $R^a$ and $R^b$ together with the nitrogen to which they are attached form a piperazino, pyrrolidino or piperidino;

for each $CR^6R^7$; $R^6$ and $R^7$ are each independently H or $CH_3$;

n is 1, 2, or 3;

X is —$OCH_3$ and Y is —$OR^3$; or Y is —$OCH_3$ and X is $OR^3$;

$R^3$ is H, $CH_3$, —$C(O)R^4$, —$C(O)OR^5$ or —$C(O)NR^cR^d$;

$R^4$ is $(C_1-C_6)$alkyl, aryl, heteroaryl, aryl(alkyl), heteroaryl(alkyl), or $(C_3-C_6)$cycloalkyl;

$R^5$ is $(C_1-C_6)$alkyl, aryl, heteroaryl, aryl(alkyl), heteroaryl(alkyl), or $(C_3-C_6)$cycloalkyl; and $R^c$ and $R^d$ are each independently H, aryl, heteroaryl, aryl(alkyl), heteroaryl(alkyl), or $(C_1-C_6)$alkyl; or $R^c$ and $R^d$ together with the nitrogen to which they are attached form a piperazino, pyrrolidino or piperidino;

or a salt or prodrug thereof.

The invention also provides a pharmaceutical composition comprising a compound of formula I, or a pharmaceutically acceptable salt or prodrug thereof, in combination with a pharmaceutically acceptable excipient, diluent or carrier.

The invention also provides a method for modulating topoisomerase activity in a mammal in need of such treatment comprising administering to the mammal (e.g. a human), a compound of formula I, or a pharmaceutically acceptable salt or prodrug thereof, effective to provide a topoisomerase modulating effect.

The invention also provides a method comprising inhibiting cancer (e.g. leukemia, non-small lung cancer, colon cancer, CNS cancer, melanoma, ovarian cancer, renal cancer, prostate cancer or breast cancer) cell growth by contacting said cancer cell in vitro or in vivo with an amount of a compound of formula I, or a pharmaceutically acceptable salt or prodrug thereof, effective to inhibit the growth of said cancer cell.

The invention also provides a method for treating cancer (e.g. leukemia, non-small lung cancer, colon cancer, CNS cancer, melanoma, ovarian cancer, renal cancer, prostate cancer or breast cancer) in a mammal (e.g. a human), comprising administering a compound of formula I, or a pharmaceutically acceptable salt or produg thereof, to the mammal.

The invention also provides a compound of formula I or a pharmaceutically acceptable salt or prodrug thereof for use in medical therapy (e.g. for use in treating cancer such as leukemia, non-small lung cancer, colon cancer, CNS cancer, melanoma, ovarian cancer, renal cancer, prostate cancer or breast cancer).

The invention also provides for the use of a compound of formula I or a pharmaceutically acceptable salt or produg thereof for the manufacture of a medicament useful for the treatment of cancer (e.g. leukemia, non-small lung cancer, colon cancer, CNS cancer, melanoma, ovarian cancer, renal cancer, prostate cancer or breast cancer) in a mammal (e.g. a human).

The invention provides a compound of formula I or a pharmaceutically acceptable salt or prodrug thereof for use in the prophylactic or therapeutic treatment of cancer (e.g. leukemia, non-small lung cancer, colon cancer, CNS cancer, melanoma, ovarian cancer, renal cancer, prostate cancer or breast cancer) in a mammal (e.g. a human).

The invention also provides processes and intermediates disclosed herein that are useful for preparing compounds of formula I or salts thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, $(C_1-C_3)$alkyl can be methyl, ethyl, propyl or isopropyl; $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl. As used herein the term "aryl($C_1-C_6$) alkyl" refers to a $(C_1-C_6)$ alkyl radical in which one or more of the hydrogen atoms of the $(C_1-C_6)$ alkyl radical is replaced with an aryl radical. As used herein the term "heteroaryl($C_1-C_6$) alkyl" refers to a $(C_1-C_6)$ alkyl radical in which one or more of the hydrogen atoms of the $(C_1-C_6)$ alkyl radical is replaced with a heteroaryl radical.

A specific group of compounds of formula I are compounds wherein A is —$C(O)NH(CR^6R^7)_nCR^1R^2NR^aR^b$ and B is H.

A specific group of compounds of formula I are compounds wherein B is —$C(O)NH(CR^6R^7)_nCR^1R^2NR^aR^b$ and A is H.

A specific value for n is 1 or 2.

A specific value for n is 1.

A specific value for $CR^6R^7$ is $CH_2$.

A specific value for $R^1$ is $(C_1-C_3)$alkyl.

A specific value for $R^2$ is $(C_1-C_3)$alkyl.

A specific group of compounds of formula I are compounds wherein $R^1$ and $R^2$ are each independently $(C_1-C_3)$ alkyl.

A specific value for $R^1$ is methyl.

A specific value for $R^2$ is methyl.

A specific group of compounds of formula I are compounds wherein $R^1$ and $R^2$ are each methyl.

A specific value for $R^a$ is H or $(C_1-C_3)$alkyl wherein $(C_1-C_3)$ alkyl may be optionally substituted with aryl or heteroaryl.

A specific value for $R^b$ is H or $(C_1-C_3)$alkyl wherein $(C_1-C_3)$ alkyl may be optionally substituted with aryl or heteroaryl.

A specific group of compounds of formula I are compounds wherein $R^a$ and $R^b$ are each independently H or $(C_1-C_3)$alkyl.

A specific group of compounds of formula I are compounds wherein $R^a$ and $R^b$ are each independently $(C_1-C_3)$alkyl.

A specific group of compounds of formula I are compounds wherein $R^a$ and $R^b$ are each methyl.

A specific value for A is —C(O)NHCH$_2$C(CH$_3$)$_2$N(CH$_3$)$_2$, —C(O)NH(CH$_2$)$_2$C(CH$_3$)$_2$N(CH$_3$)$_2$ or —C(O)NH(CH$_2$)$_3$C(CH$_3$)$_2$N(CH$_3$)$_2$.

A specific value for B is —C(O)NHCH$_2$C(CH$_3$)$_2$N(CH$_3$)$_2$, —C(O)NHCH$_2$C(CH$_3$)$_2$N(CH$_2$Ph)$_2$, —C(O)NHCH$_2$C(CH$_3$)$_2$NH$_2$, —C(O)NH(CH$_2$)$_2$C(CH$_3$)$_2$N(CH$_3$)$_2$ or —C(O)NH(CH$_2$)$_3$C(CH$_3$)$_2$N(CH$_3$)$_2$.

A specific group of compounds of formula I are compounds wherein X is —OCH$_3$ and Y is —OR$^3$.

A specific group of compounds of formula I are compounds wherein Y is —OCH$_3$ and X is —OR$^3$.

A specific value for $R^3$ is H, CH$_3$, —C(O)R$^4$, —C(O)OR$^5$ or —C(O)NR$^c$R$^d$.

A specific value for $R^3$ is —C(O)R$^4$, —C(O)OR$^5$ or —C(O)NR$^c$R$^d$.

A specific value for $R^3$ is H.
A specific value for $R^3$ is CH$_3$.
A specific value for $R^4$ is $(C_1-C_6)$alkyl.
A specific value for $R^5$ is $(C_1-C_6)$alkyl.
A specific value for $R^c$ is H or $(C_1-C_6)$alkyl.
A specific value for $R^d$ is H or $(C_1-C_6)$alkyl.

A specific compound of formula I is the compound 2,3-dimethoxy-N-(2-(dimethylamino)-2-methylpropyl)-8,9-methylenedioxybenzo[i]phenanthridine-12-carboxamide; or N-(2-(dibenzylamino)-2-methylpropyl)-2,3-dimethoxy-8,9-methylenedioxybenzo[i]phenanthridine-12-carboxamide; or N-(2-amino-2-methylpropyl)-2,3-dimethoxy-8,9-methylenedioxybenzo[i]phenanthridine-12-carboxamide; or 2,3-dimethoxy-8,9-methylenedioxybenzo[i]phenanthridine-11-carboxylic acid 2-(dimethylamino)-2-methylpropylamide; or 2,3-dimethoxy-N-(3-(dimethylamino)-3-methylbutyl)-8,9-methylenedioxybenzo[i]phenanthridine-12-carboxamide; or 2,3-dimethoxy-N-(4-(dimethylamino)-4-methylpentyl)-8,9-methylenedioxybenzo[i]phenanthridine-12-carboxamide; 2,3-dimethoxy-8,9-methylenedioxybenzo[i]phenanthridine-11-carboxylic acid 3-(dimethylamino)-3-methylbutylamide; 2,3-dimethoxy-8,9-methylenedioxybenzo[i]phenanthridine-11-carboxylic acid 4-(dimethylamino)-4-methylpentylamide or a salt or prodrug thereof.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself.

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases.

Certain compounds of formula I can function as prodrugs for other compounds of formula I and are thus embodiments of the invention. For example, a compound of formula I wherein $R^3$ is —C(O)R$^4$, —C(O)OR$^5$, or —C(O)NR$^c$R$^d$ can function as a prodrug for a corresponding compound of formula I wherein $R^3$ is hydrogen.

Particularly useful prodrugs are those that are linked through a phenolic functional group. Accordingly, in one embodiment the invention provides a prodrug comprising a compound of formula I that releases a phenol of a compound of formula I. In another embodiment the invention provides prodrugs that comprise a targeting moiety (e.g. an antibody).

Processes for preparing compounds of formula I are provided as further embodiments of the invention and are illustrated by the following procedures in which the meanings of the generic radicals are as given above unless otherwise qualified.

Representative compounds of the invention were prepared as illustrated below in Schemes 1-6.

Scheme 1: Preparation of compounds 31, 32 and 33

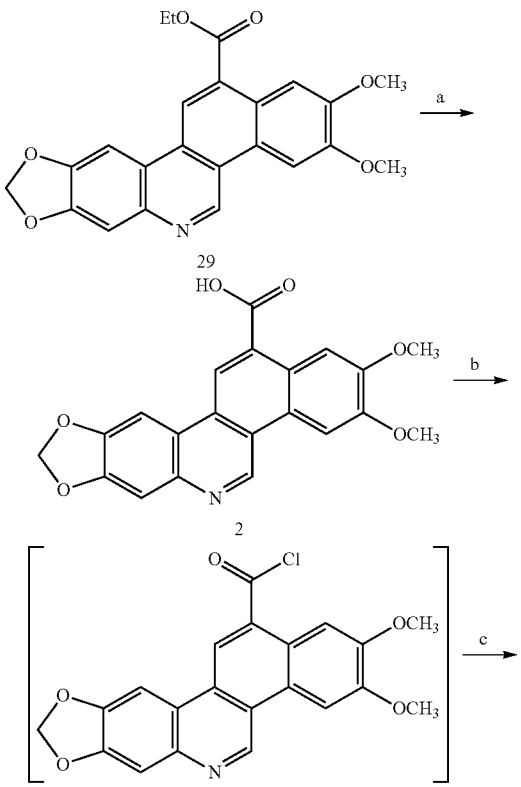

7
-continued
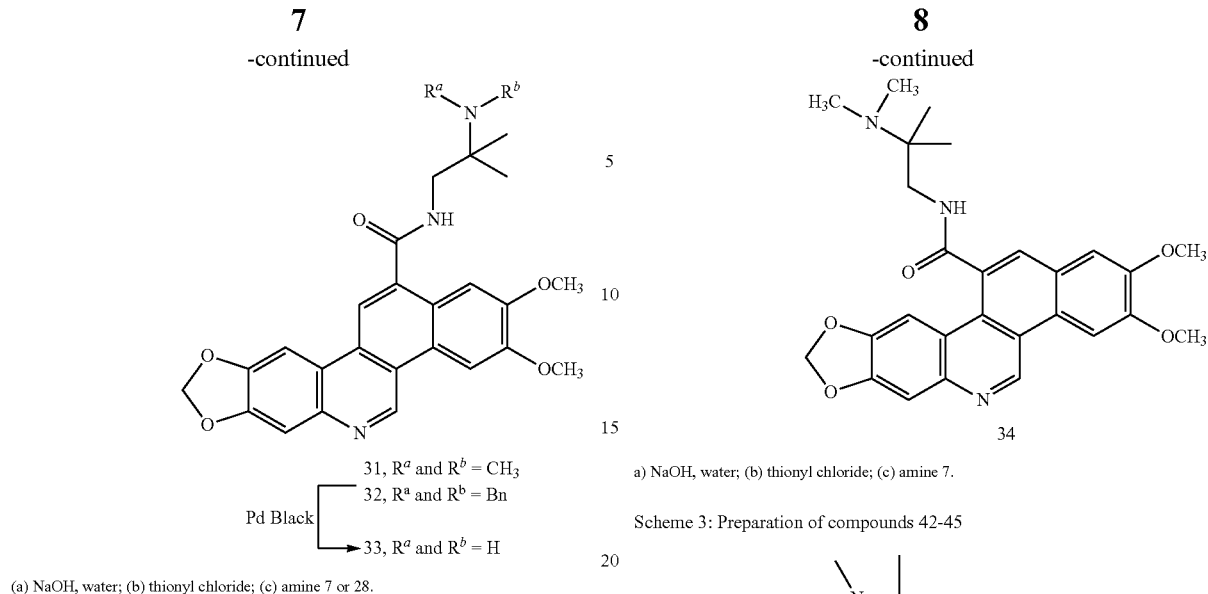
31, $R^a$ and $R^b$ = $CH_3$
32, $R^a$ and $R^b$ = Bn
    Pd Black
→ 33, $R^a$ and $R^b$ = H
(a) NaOH, water; (b) thionyl chloride; (c) amine 7 or 28.
Scheme 2: Preparation of compound 34
8
-continued
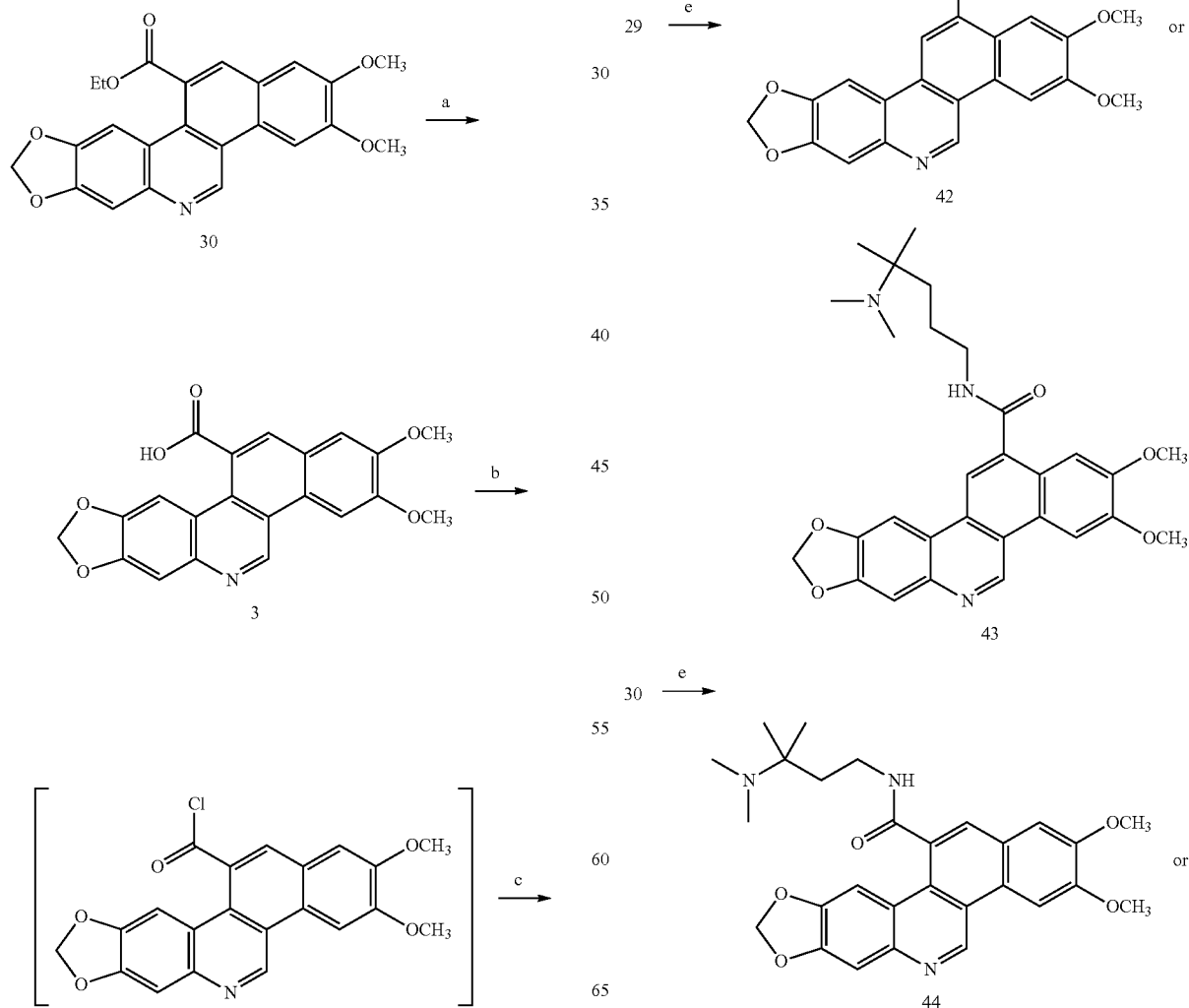
a) NaOH, water; (b) thionyl chloride; (c) amine 7.
Scheme 3: Preparation of compounds 42-45

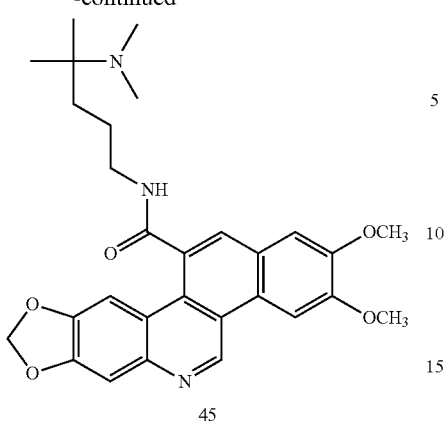

45

(e) NaOH, water; then thionyl chloride followed by amine 40 or 41.

Scheme 4: Preparation of amine intermediate 28

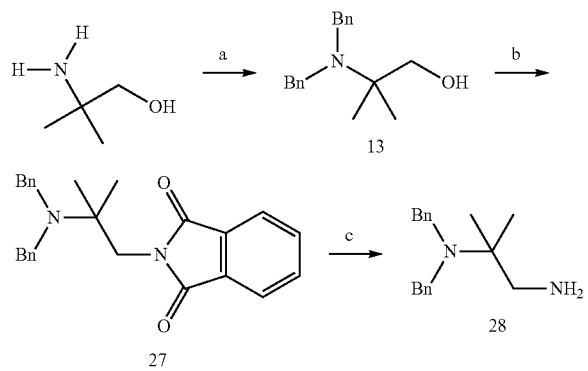

a) BnBr, K₂CO₃, acetone; (b) PPh₃, phthalimide, DEAD, THF
(c) NH₂NH₂, EtOH, 60° C.

Scheme 5: Preparation of amine intermediate 7

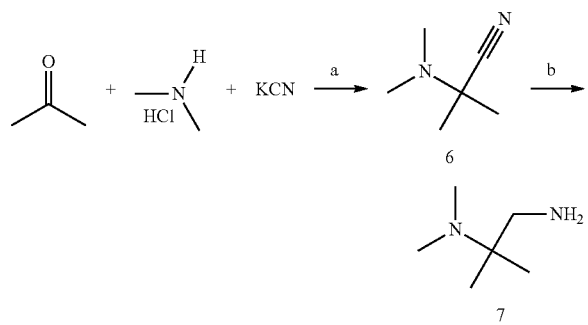

(a) Water; (b) LAH, ether.

Scheme 6: Preparation of amine intermediates 40 and 41

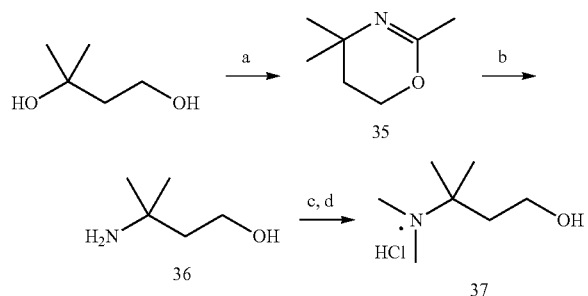

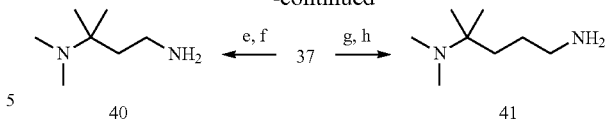

(a) Acetonitrile, sulfuric acid; (b) NaOH, water; (c) Formic acid, formaldehyde;
(d) Thionyl chloride, chloroform; (e) Potassium phthalimide, DMF;
(f) Hydrazine, EtOH; (g) KCN, 18-crown-6, acetonitrile; (h) LAH, ether.

A compound of formula I wherein B is —C(O)NH(CR⁶R⁷)ₙCR¹R²NRᵃRᵇ and A is hydrogen can be prepared by converting a corresponding acid of formula 2:

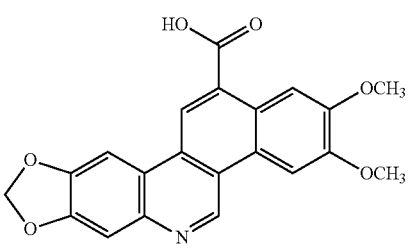

to the compound of formula I, for example by coupling the acid of formula 2 with an amine to provide a compound of formula I. Thus, the intermediate acid of formula 2 is useful for preparing a compound of formula I.

A compound of formula I wherein A is —C(O)NH(CR⁶R⁷)ₙCR¹R²NRᵃRᵇ and B is hydrogen can be prepared by converting a corresponding acid of formula 3:

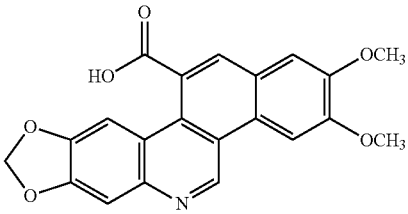

to the compound of formula I, for example by coupling the acid of formula 3 with an amine to provide a compound of formula I. Thus, the intermediate acid of formula 3 is useful for preparing a compound of formula I.

Accordingly, the invention provides a method:
a) for preparing a compound of formula I wherein B is —C(O)NH(CR⁶R⁷)ₙCR¹R²NRᵃRᵇ comprising treating a compound of formula 2 with an appropriate amine (e.g. H₂N(CR⁶R⁷)ₙCR¹R²NRᵃRᵇ) to provide the compound of formula I.
b) for preparing a compound of formula I wherein A is —C(O)NH(CR⁶R⁷)ₙCR¹R²NRᵃRᵇ comprising treating a compound of formula 3 with an appropriate amine (e.g. H₂N(CR⁶R⁷)ₙCR¹R²NRᵃRᵇ) to provide the compound of formula I.
c) for preparing a compound of formula I comprising deprotecting a corresponding compound bearing one or more protecting groups to provide the compound of formula I.
d) for preparing a salt of a compound of formula I comprising treating a compound of formula I with an acid (e.g. an organic acid or inorganic acid) or base (e.g. an alkali base or alkaline base) to provide the salt of the compound of formula I.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 100 mg/kg, e.g., from about 0.5 to about 75 mg/kg of body weight per day, such as 1 to about 50 mg per kilogram body weight of the recipient per day, preferably in the range of 1 to 20 mg/kg/day.

The compound is conveniently formulated in unit dosage form; for example, containing 0.5 to 100 mg, conveniently 1 to 75 mg, most conveniently, 0.5 to 25 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The ability of a compound of the invention to effect topoisomerase I or II mediated DNA cleavage can be determined using pharmacological models that are well known in the art, for example, using a model like Test A described below.

Test A. Topoisomerase I—Mediated DNA Cleavage Assay

Human topoisomerase I was expressed in *Escherichia coli* and isolated as a recombinant fusion protein using a T7 expression system as described previously (31). Plasmid YepG was also purified by the alkali lysis method followed by phenol deproteination and CsCl/ethidium isopycnic centrifugation method as described (32). The 3' end labeling of the plasmid was accomplished by digestion with a restriction enzyme followed by end filling with Klenow polymerase as previously described (33). The cleavage assays were performed as previously reported (34,35). The drug and the DNA in presence of topoisomerase I was incubated for 30 min at room temperature. The reactions were terminated by the addition of 5 μL of 5% SDS and 1 mg/mL protein kinase K with an additional 1 h of incubation at 37° C. Samples were then alkali denatured by the addition of NaOH, EDTA, sucrose, and bromophenol blue to final concentrations of 75 mM, 2.5%, and 0.05 mg/mL, respectively, prior to loading onto a neutral agarose gel. After development of the gels, typically 24-h exposure was used to obtain autoradiograms outlining the extent of DNA fragmentation. Topoisomerase I-mediated DNA cleavage values are reported as Relative Effective Concentration (REC). The REC value reflects the concentrations relative to camptothecin, whose value is arbitrarily assumed as 0.2, that is able to produce the same 10% cleavage on the plasmid DNA in the presence of human topoisomerase I. Results for the assay for representative compounds of the invention of formula I along with comparison compounds are shown in Table 1. The data demonstrate that representative compounds of the invention target topoisomerase I.

TABLE 1

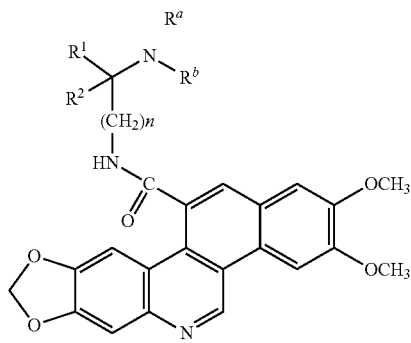

C

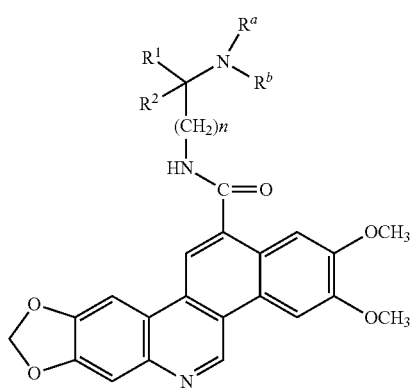

D

| Compound | | | | TOP1 Mediated DNA Cleavage (REC Value) |
|---|---|---|---|---|
| | n | $R^a$ and $R^b$ | $R^1$ and $R^2$ | |
| 216 | C | 1 | $CH_3$ | H | 0.2 |
| 34 | C | 1 | $CH_3$ | $CH_3$ | 0.09 |
| 44 | C | 2 | $CH_3$ | $CH_3$ | 0.4 |
| 45 | C | 3 | $CH_3$ | $CH_3$ | 2.5 |
| 206 | D | 1 | $CH_3$ | H | 0.1 |
| 31 | D | 1 | $CH_3$ | $CH_3$ | 0.1 |
| 32 | D | 1 | Bn | $CH_3$ | 1.5 |
| 33 | D | 1 | H | $CH_3$ | 1.1 |
| 48 | D | 2 | $CH_3$ | H | 3 |
| 42 | D | 2 | $CH_3$ | $CH_3$ | 2.3 |
| 43 | D | 3 | $CH_3$ | $CH_3$ | 3.4 |
| CPT | | | | | 0.2 |
| Topotecan | | | | | 1.0 |

A similar assay can be used to evaluate the ability of a compound of the invention to effect topoisomerase II mediated DNA cleavage by replacing the human topoisomerase I used in Test A with a suitable topoisomerase II.

The cytotoxic effects of a compound of the invention can be determined using pharmacological models that are well known in the art, for example, using a model like Test B described below.

Test B. Cytotoxic Assays (Cancer Cell Lines and Efflux Transporter Cell Lines)

The cytotoxicity was determined using the MTT-microtiter plate tetrazolinium cytotoxicity assay (MTA). The human lymphoblast RPMI 8402 and its camptothecin-resistant variant cell line, CPT-K5 was provided by Dr. Toshiwo Andoh (Aichi Cancer Center Research Institute, Nagoya, Japan). (36) The P388 mouse leukemia cell line and its CPT-resistant TOP1-deficient variant P388/CPT45 (37) were obtained from Michael R. Mattern and Randal K. Johnson (GlaxoSmithKline, King of Prussia, Pa.). The KB3-1 cell line and its multidrug-resistant variant KBV-1 (38) were obtained from K. V. Chin (The Cancer Institute of New Jersey, New Brunswick, N.J.). The KBH5.0 cell line as noted previously (21) was derived from KB3-1 by stepwise selection against Hoechst 33342. The cytotoxicity assay was performed using 96-well microtiter plates. Cells were grown in suspension at 37° C. in 5% $CO_2$ and maintained by regular passage in RPMI medium supplemented with 10% heat inactivated fetal bovine serum, L-glutamine (2 mM), penicillin (100 U/mL), and Streptomycin (0.1 mg/mL). For determination of $IC_{50}$, cells were exposed continuously for FOUR days to varying concentrations of drug, and MTT assays were performed at the end of the fourth day. Each assay was performed with a control that did not contain any drug. All assays were performed at least twice in six replicate wells.

Experimental results from Test B for representative compounds of the invention which are compounds of formula I and comparator compounds are shown in the Table 2 below. These results demonstrate that compounds of the invention can function as cytotoxic agents against tumor cell lines. Accordingly compounds of the invention of formula I may be useful as therapeutic agents for the treatment of cancer (e.g. leukemia, non-small lung cancer, colon cancer, CNS cancer, melanoma, ovarian cancer, renal cancer, prostate cancer or breast cancer) and to treat tumors that are that are resistant to other chemotherapeutic agents.

Additionally, compounds of the invention may be useful as pharmacological tools for the further investigation of topoisomerase I function.

TABLE 2

C

[Structure of compound C showing chromene-fused ring system with $R^1$, $R^2$, $R^a$, $R^b$ substituents, $(CH_2)n$ linker, HN-C(=O) amide, and two $OCH_3$ groups]

D

[Structure of compound D showing similar ring system with $R^1$, $R^2$, $R^a$, $R^b$ substituents, $(CH_2)n$ linker, HN-C=O amide, and two $OCH_3$ groups]

| Compound | | | | Cytotoxicity $IC_{50}$ (µM) | | | |
|---|---|---|---|---|---|---|---|
| | n | $R^a$ and $R^b$ | $R^1$ and $R^2$ | RPMI8402 | CPT-K5 | P388 | P388/CPT45 |
| 216 | C | 1 | $CH_3$ | H | 0.035 | 0.63 | 0.015 | 0.26 |
| 34 | C | 1 | $CH_3$ | $CH_3$ | 0.003 | 0.5 | 0.002 | 0.23 |
| 44 | C | 2 | $CH_3$ | $CH_3$ | 0.15 | 5 | 0.27 | 1.27 |

TABLE 2-continued

| 45 | C | 3 | $CH_3$ | $CH_3$ | 0.28 | 5.5 | 0.28 | 3.25 |
|---|---|---|---|---|---|---|---|---|
| 206 | D | 1 | $CH_3$ | H | 0.003 | 1.0 | 0.003 | 0.32 |
| 31 | D | 1 | $CH_3$ | $CH_3$ | 0.002 | 0.79 | 0.002 | 0.25 |
| 32 | D | 1 | Bn | $CH_3$ | 0.06 | 5.0 | 0.03 | 1.3 |
| 33 | D | 1 | H | $CH_3$ | 0.01 | 2.2 | 0.02 | 0.76 |
| 48 | D | 2 | $CH_3$ | H | 0.05 | 2.0 | 0.03 | 0.34 |
| 42 | D | 2 | $CH_3$ | $CH_3$ | 0.025 | 2.07 | 0.09 | 0.53 |
| 43 | D | 3 | $CH_3$ | $CH_3$ | 0.16 | 3.0 | 0.18 | 0.4 |
| CPT | | | | | 0.006 | >10 | 0.014 | >10 |
| Topotecan | | | | | 0.021 | >10 | 0.045 | >10 |

The ability of a compound of the invention to be actively transported can be determined using pharmacological models that are well known in the art, for example, using a model like the test described below.

The cytotoxicity of the representative compounds of the invention were also tested on cell line KB3-1 (parent cell line), KBV-1 (a variant that overexpresses efflux transporter MDR1) and KBH5.0 (a variant that overexpresses BCRP). The data is tabulated in Table 3. Differences in the relative cytotoxicity between the parent and variant cell lines may be indicative of a compound that is a substrate for an efflux transporter. These data suggest that all of the compounds tested may be substrates to varying degrees for MDR1 and that compounds 31 and 34 are not substrates for BCRP. Accordingly, compounds of the invention of formula I may be useful to treat tumors that are resistant to other anticancer agents, especially anticancer agents that are susceptible to efflux by BCRP (e.g. anthracyclines, mitoxantrone, topotecan, irinotecan, bisanthrone, doxorubicin, daunorubicin, and epirubin.

TABLE 3

| Compd | KB3-1 | KBV-1 | KBH5.0 |
|---|---|---|---|
| 216 | 0.027 | 1.4 | 0.2 |
| 34 | 0.003 | 0.065 | 0.01 |
| 44 | 0.24 | >10 | 0.47 |
| 45 | 0.21 | >10 | 0.85 |
| 206 | 0.005 | 0.22 | 0.06 |
| 31 | 0.001 | 0.03 | 0.004 |
| 32 | 0.02 | 2.9 | 0.6 |
| 33 | 0.004 | 0.48 | 0.19 |
| 42 | 0.05 | 2.5 | 0.16 |
| 43 | 0.25 | 2.8 | 0.6 |
| CPT | 0.015 | 0.025 | 0.026 |
| Topotecan | 0.04 | 0.44 | 0.44 |

The in vivo antitumor activity of a compound of the invention can be determined using pharmacological models that are well known in the art, for example, using a model like Test C described below.

Test C. Human Tumor Xenograft Assay

Bioassays were performed using female NCR/NU NU mice of approximately 9 weeks of age as obtained from Taconic Farms, Inc. (Germantown, N.Y., USA). Mice were housed 4 per cage in laminar flow HEPA filtered microisolator caging (Allentown Caging Equipment Co., Allentown, N.J., USA). Mice were fed Purina autoclavable breeder chow #5021 and given drinking water, purified by reverse-osmosis, ad libitum. Five days after arrival within the animal facility, the mice were inoculated on the right flank with $1.5 \times 10^6$ MDA-MB-435 tumor cells in 0.1 mL of RPMI 1640 Media by sc injection (25 gauge needlex⅝"). The MDA-MB-435 cells were grown in 75 $cm^2$ flasks using RPMI 1640 Media and 10% fetal bovine serum. Tumors were of sufficient size at 19-20 days after inoculation. Tumor-bearing mice were evenly matched in each experimental group based on tumor volume. Tumor volume was calculated by measuring the tumor with a microcaliper. The length (l) is the maximum two dimensional distance of the tumor and the width (w) is the maximum distance perpendicular to this length measured in mm. Tumor volume was calculated using the formula (l*w$^2$)/2. Every mouse in this study was weighed individually on a daily basis. Dose adjustments for each experimental group, as indicated in Table 4, were made throughout the study based upon the effect or lack of an effect of treatment on average body weights. Tumor volume was determined for each individual mouse every other day. Compound 31, the α,α-dimethyl analog of 206, was better tolerated and significantly more effective than 206 as an antitumor agent as indicated in Table 4.

TABLE 4

In vivo Antitumor Activity of the α,α-dimethyl analog 31
in Athymic Nude Mice with MDA-MB-435 Human Tumor Xenografts

| Compd. | Route | Average tumor volume (mm$^3$) | | | | | | | Total dose (mg/kg)/mouse |
| --- | --- | --- | --- | --- | --- | --- | --- | --- | --- |
| | | Day 7 | Day 14 | Day 21 | Day 28 | Day 35 | Day 42 | Day 49 | |
| 31 | I.P.$^a$ | 96 | 122 | 147 | 191 | 201 | 227 | 248 | 152.82 mg/kg |
| 31 | P.O.$^b$ | 93 | 112 | 121 | 147 | 164 | 252 | 301 | 208.13 mg/kg |
| 206 | I.P.$^d$ | 63 | 101 | 191 | 423 | 898 | 1294 | 1382 | 131.25 mg/kg |
| Vehicle | I.P.$^c$ | 84 | 143 | 219 | 488 | 871 | 1197 | 1238 | |

$^a$Initial dose was 3.75 mg/kg qd × 5/week for 4.5 weeks. Administration was adjusted to 4.875 mg/kg qd × 5/week for half a week and was increased to 5.625 mg/kg qd × 5/week for 2 weeks in view of gain weight;
$^b$Initial dose was 5.625 mg/kg qd × 5/week for 5 weeks and was increased to 6.75 mg/kg qd × 5/week for 2 weeks.
$^c$Vehicle consisted of 0.1% citrate in H$_2$O. × 5/week for 2 weeks.
$^d$Initial dose was 5.625 mg/kg qd × 5/week for 5 weeks and was increased to 6.75 mg/kg qd × 5/week for 2 weeks.

Topoisomerase inhibitors are also known to possess antibacterial, antifungal, antiprotozoal, antihelmetic, and antiviral activity. Accordingly, the topoisomerase inhibitors of the invention may also be useful as antibacterial, antifungal, antipsoritic (psoriasis) antiprotozoal, antihelmetic, or antiviral agents. In particular, compounds of the invention that demonstrate little or no activity as mammalian topoisomerase I poisons, because of the possibility of similar molecular mechanism of action, could be highly active and selective antibacterial, antifungal, antiprotozoal, antihelmetic, or antiviral agents. Thus, certain compounds of the invention may be particularly useful as systemic antibacterial, antifungal, antiprotozoal, antihelmetic, or antiviral agents in mammals. The invention also provides the use of a compound of the invention for the manufacture of a medicament useful for producing an antibacterial, antifungal, antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

EXAMPLES

The invention will now be illustrated by the following non-limiting Examples.

Example 1

Synthesis of Compound 31

2,3-Dimethoxy-N-(2-(dimethylamino)-2-methylpropyl)-8,9-methylene-dioxybenzo[i]phenanthridine-12-carboxamide (31). To a suspension of acid 2 (450 mg, 1.2 mmol) (Zhu, S. Ruchelman, A. L., Zhou, N., Liu, A. A., Liu, L, F., and LaVoie, E. J., *Bioorg. Med. Chem.*, 13, (2005) 6782-6794) in anhydrous CHCl$_3$ (250 mL) was added SOCl$_2$ (18 mL, 247 mmol) and refluxed for 5 hours. The reaction mixture was concentrated on rotavap and dried under high vacuum for 1 hour. The solid residue was suspended in a mixture of anhydrous DCM (150 mL) and TEA (10 mL, 72 mmol) and stirred for 2 hours. Then it was charged with 2-dimethylamino-2-methylpropylamine (7) (2.5 g, 21 mmol) and stirred for 1 hour, diluted with sat. NaHCO$_3$ solution and extracted. Organic layer was dried, filtered, concentrated and the residue was purified by flash chromatography to yield 31 in 84%; mp 274-276° C.; IR (CHCl$_3$) 3384, 1663; $^1$H NMR (CDCl$_3$) δ 1.23 (s, 6H), 2.31 (s, 6H), 3.62 (d, 2H, J=5), 4.04 (s, 3H), 4.15 (s, 3H), 6.13 (s, 2H), 7.28 (bs, 1H), 7.56 (s, 1H), 7.67 (s, 1H), 7.73 (s, 1H), 8.02 (s, 1H), 8.17 (s, 1H), 9.72 (s, 1H); $^{13}$C NMR (CDCl$_3$) δ 19.6, 37.4, 46.8, 55.0, 55.1, 98.2, 101.1, 105.1, 105.6, 116.4, 119.7, 119.9, 124.7, 128.5, 135.5, 140.8, 143.8, 147.6, 148.5, 148.9, 149.6, 169.2; HRMS calcd for C$_{27}$H$_{29}$N$_3$O$_5$Li: 482.2267. found 482.2278.

The required amine, 2-dimethylamino-2-methylpropylamine (7), was prepared as follows.

a) 2-Dimethylamino-2-methylpropionitrile (6)

A solution of KCN (13 g, 200 mmol) in 100 mL water was added to a stirred, cooled suspension of dimethylamine hydrochloride (16.3 g, 200 mmol) and acetone (6.96 g, 120 mmol). The mixture was stirred overnight at room temperature and then extracted with ether (50 mL×3). The organic layer was dried over Na$_2$SO$_4$ and then concentrated under vacuum to provide product 9.32 g in 92% yield as a colorless, water-like liquid. $^1$H NMR (CDCl$_3$) δ 1.42 (s, 6H), 2.36 (s, 6H); $^{13}$C NMR (CDCl$_3$) δ 26.8, 40.8, 57.2, 119.7.

b) 2-Dimethylamino-2-methylpropylamine (7)

To a suspension of LAH (3.8 g, 100 mmol) in 150 mL ether was added a solution of 6 (5.6 g, 50 mmol) in ether (12 mL) dropwise at −5° C. The reaction was stirred at room temperature for 5 hours and then cooled down to −5° C. 4 mL Water, 4 mL 15% NaOH and 12 mL water were added sequentially. The resulting mixture was filtered and filtrate was extracted with water, brine and dried over $Na_2SO_4$. The organic extract was concentrated under vacuum and then distilled to afford a colorless water-like liquid 5.3 g in 91% yield. bp 145-147° C.; $^1$H NMR ($CDCl_3$) δ 0.95 (s, 6H), 1.38 (s, 2H), 2.20 (s, 6H), 2.56 (s, 2H); $^{13}$C NMR ($CDCl_3$) δ 19.2, 37.5, 49.9, 55.8.

Example 2

Synthesis of Compound 32

N-(2-(Dibenzylamino)-2-methylpropyl)-2,3-dimethoxy-8,9-methylene-dioxybenzo[i]phenanthridine-12-carboxamide (32)

To a suspension of acid 2 (97 mg, 0.26 mmol) in DCM (15 mL) was added excess of $SOCl_2$ (5 mL, 69 mmol) and refluxed for 3 h. Reaction mixture was concentrated under vacuum to complete dryness. The residue was suspended in DCM (10 mL) and refluxed with 2-dibenzylamino-2-methyl-propylamine (28) (400 mg, 1.5 mmol) for 2 h. Reaction mixture was washed with water (20 mL), brine (20 mL), dried ($Na_2SO_4$) and filtered. Solvent was evaporated on rotavap and the crude was purified by flash chromatography get a light yellow solid 32 in 60% yield; mp 257-259° C.; IR ($CHCl_3$) 1651; $^1$H NMR ($CDCl_3$) δ 1.54 (s, 6H), 3.84 (d, 2H, J=5), 3.99 (s, 4H), 4.14 (s, 3H), 4.39 (s, 3H), 6.43 (s, 2H), 7.22 (m, 7H), 7.34 (m, 4H), 7.86 (s, 1H), 7.94 (s, 1H), 7.98 (s, 1H), 8.28 (s, 1H), 8.34 (s, 1H), 10.1 (s, 1H); $^{13}$C NMR ($CDCl_3$) δ 22.8, 48.2, 53.7, 56.0, 56.3, 99.5, 102.1, 102.3, 106.4, 116.7, 121.0, 124.1, 126.0, 127.1, 128.5, 137.5, 141.1, 144.3, 149.0, 150.2, 151.0, 169.3; HRMS calcd for $C_{39}H_{37}N_3O_5Li$: 634.2893. found 634.2879.

The required amine, 2-dibenzylamino-2-methyl-propylamine (28), was prepared as follows.

a) 2-Dibenzylamino-2-methylpropan-1-ol (13)

To a solution of 2-amino-2-methylpropan-1-ol (5.1 mL, 53.3 mmol) in acetone and water (4:1, 100 mL) were added benzyl bromide and potassium carbonate (14.74 g, 106.6 mmol). The resulting reaction mixture was heated to reflux for 40 h. The reaction mixture was evaporated and partitioned in dichloromethane and water. The organic layer was then washed with brine (100 mL), dried ($Mg_2SO_4$), and evaporated, yielding 15 g of 13 in 98% yield as a light yellow solid; $^1$H NMR ($CDCl_3$) δ 1.13 (s, 6H), 3.02 (s, 1H), 3.47 (s, 2H), 3.76 (s, 4H), 7.17-7.28 (m, 10H).

b) 2-(Dibenzylamino)-2-methylpropyl)isoindoline-1,3-dione (27)

To a solution of triphenylphosphine (1.96 g, 7.5 mmol), phthalimide (1.1 g, 7.5 mmol), and 2-dibenzylamino-2-methylpropan-1-ol (1.35 g, 5.0 mmol) in anhydrous THF was added DEAD (1.3 g, 7.5 mmol) in THF dropwise as not to allow the reaction to exceed room temperature. The reaction was stirred at room temperature for 2 hours under a nitrogen atmosphere. The reaction mixture was concentrated under reduced pressure and the residue subjected to flash column chromatography using 20-30% $CHCl_3$ in hexanes to provide 1.25 g (62.5% yield) of 27.

c) 2-(2-(Dibenzylamino)-2-methylpropylamine (28)

To a solution of 2-(dibenzylamino)-2-methylpropyl)isoindoline-1,3-dione (1.25 g. 3.14 mmol) in absolute ethanol (6 ml) and benzene (4 ml) was added 0.54 ml of acetic acid (9.42 mmol) followed by 50% aqueous hydrazine (0.46 ml, 9.42 mmol) and the mixture stirred at reflux for 8 hours. The resulting solid residue was filtered and the filtrate concentrated under reduced pressure. The residue was dissolved in EtOAc and extracted twice with 1.0 N HCl. The aqueous layer was separated, made basic with 5% NaOH, and extracted with EtOAc. The organic layer was concentrated under reduce pressure and purified by flash column chromatography using a gradient from 1-2% MeOH in $CHCl_3$ to provide 474 mg (56.4% yield) of 28.

Example 3

Synthesis of Compound 33

N-(2-Amino-2-methylpropyl)-2,3-dimethoxy-8,9-methylenedioxybenzo[i]phenanthridine-12-carboxamide (33)

To a solution of 32 (22 mg, 0.03 mmol) in acetic acid (5 mL) and formic acid (1 mL) was added Pd black (20 mg) and stirred at room temperature for 2 hours. Reaction mixture was filtered through celite, concentrated under reduced pressure, basified with 10% NaOH (4 mL) and extracted with 2% methanol in chloroform (60 mL). Organic layer was dried over $Na_2SO_4$, filtered and concentrated. Crude was purified by a short column to yield a light yellow solid 155 in 58% yield; mp 269-271° C. (dec); IR ($CHCl_3$) 3373, 1635; $^1$H NMR ($CDCl_3$) δ 1.23 (s, 6H), 3.83 (bs, 2H), 4.02 (s, 3H), 4.16 (s, 3H), 6.12 (s, 2H), 7.35 (s, 1H), 7.75 (s, 1H), 8.09 (s, 1H), 8.51 (s, 1H), 9.80 (s, 1H); HRMS calcd for $C_{25}H_{25}N_3O_5Li$: 454.1954. found 454.1943.

Example 4

Synthesis of Compound 34

2,3-Dimethoxy-8,9-methylenedioxybenzo[i]phenanthridine-11-carboxylic acid 2-(dimethylamino)-2-methylpropylamide (34)

A mixture of acid 3 (15 mg, 0.037 mmol) (U.S. Pat. No. 7,208,492) in 10% NaOH (5 mL) and ethanol (10 mL) was heated to reflux with stirring for 1 hour. The reaction mixture was acidified with 2N HCl to pH=4, and then evaporated to dryness. The residue was suspended in 10 mL dichloromethane and 0.5 mL thionyl chloride was added. The resulting reaction mixture was refluxed for 2 h and then concentrated. The reaction residue was again suspended in dichloromethane and 0.5 mL triethylamine was added. After 15 min, 0.5 mL 2-dimethylamino-2-methylpropylamine (7) was added and the resulting reaction mixture was refluxed for 1 h. The organic solvent and excess amine were removed under reduced pressure and the residue was chromatographed in 20:1 $CH_2Cl_2$/MeOH to provide a off-white powder 11 mg in 62% yield; mp 222-225° C.; IR (KBr) 1642; $^1$H NMR ($CDCl_3$) δ 1.26 (s, 6H), 2.15 (s, 6H), 3.55 (d, 2H, J=4.8), 4.05 (s, 3H), 4.15 (s, 3H), 6.10 (s, 2H), 6.93 (br, 1H), 7.25

(s, 1H), 7.50 (s, 1H), 7.83 (s, 1H), 7.97 (s, 1H), 8.05 (s, 1H), 9.85 (s, 1H); $^{13}$C NMR (CDCl$_3$) δ 19.8, 37.2, 47.8, 54.7, 55.2, 55.3, 100.9, 101.2, 101.8, 106.3, 107.2, 118.6, 120.6, 124.9, 125.2, 126.7, 129.6, 129.7, 142.6, 144.5, 147.0, 148.1, 149.3, 150.5, 171.0; HRMS calcd for C$_{27}$H$_{29}$N$_3$O$_5$H, 476.2185. found 476.2180.

Example 5

Synthesis of Compound 42

2,3-Dimethoxy-N-(3-(dimethylamino)-3-methylbutyl)-8,9-methylenedioxybenzo[i]phenanthridine-12-carboxamide (42)

Compound 42 was synthesized from acid 2 using a similar procedure for 34 except the amine used was 2-dimethylamino-2-methylbutylamine (40). Light yellow solid 17 mg was obtained in 71% yield; mp 228-230° C.; IR (KBr) 1636; $^1$H NMR (CDCl$_3$) δ 1.54 (s, 6H), 2.33 (t, 2H, J=8.4), 2.83 (s, 6H), 3.75 (t, 2H, J=8.4), 4.03 (s, 3H), 4.13 (s, 3H), 6.14 (s, 2H), 7.32 (s, 1H), 7.81 (s, 1H), 7.92 (s, 1H), 7.95 (s, 1H), 8.34 (s, 1H), 9.70 (s, 1H); $^{13}$C NMR (CDCl$_3$) δ 20.5, 34.6, 35.4, 36.7, 54.9, 55.2, 63.5, 97.4, 98.5, 101.3, 101.7, 102.7, 105.3, 116.5, 119.5, 120.3, 123.0, 136.3, 137.4, 141.8, 148.6, 149.3, 150.2, 168.8; HRMS calcd for C$_{28}$H$_{31}$N$_3$O$_5$H: 490.2336. found 490.2339.

The required amine, 2-dimethylamino-2-methylbutylamine (40) was prepared as follows.

a) 4-Chloro-N,N,2-trimethylbutan-2-amine, hydrochloride (37)

To the primary amine 36 (3 g, 29 mmol) was added formic acid (2.86 mL, 73 mmol) and formalin (5.43 mL, 73 mmol) slowly. The resulting reaction mixture was heated up to reflux for 5 h, then cooled to room temperature and basified by excess KOH. The mixture was extracted with ether (100 mL×2). The ether layer was dried over Na$_2$SO$_4$ and concentrated to give a colorless oil. The oil (1 g, 7.63 mmol) was dissolved in chloroform (15 mL) and thionyl chloride (2.78 mL, 38.2 mmol) was added. The reaction mixture was heated to reflux for 2 hours, evaporated to dryness, and then triturated by ether. The resulting off-white solid (1.35 g, 95% yield) was dried in vacuum over night. $^1$H NMR (CDCl$_3$) δ 1.41 (s, 6H), 2.20 (t, 2H, J=8.0), 2.65 (s, 3H), 2.68 (s, 3H), 3.62 (t, 2H, J=8.0); $^{13}$C NMR (CDCl$_3$) δ 21.9, 37.6, 38.8, 39.6, 63.7.

b) 2-Dimethylamino-2-methylbutylamine (40)

To a solution of 37 (1 g, 5.4 mmol) in DMF (10 mL) was added potassium phthalimide (2 g, 10.8 mmol) and the resulting reaction mixture was heated up to 70° C. for 24 hours. The reaction mixture was quenched by 1 mL water and concentrated to dryness. The residue was dissolved in chloroform and washed with water, extracted with 2 N HCl and then basified. The precipitate was again extracted by chloroform (100 mL×2). The concentrate of organic solution finally afforded a yellow oil 700 mg, in 50% yield. The yellow oil (700 mg, 2.7 mmol) was heated with hydrazine (0.8 mL, 16.2 mmol) in ethanol (100 ml) to 60° C. for 18 hours. The reaction mixture was cooled, filtered and the filtrate was concentrated carefully to give a colorless oil 200 mg, in 57% yield. $^1$H NMR (CDCl$_3$) δ 1.01 (s, 6H), 1.47 (s, br, 1H), 1.56 (t, 2H, J=8.0), 2.22 (s, 6H), 2.76 (t, 2H, J=8.0); $^{13}$C NMR (CDCl$_3$) δ 21.9, 37.1, 37.6, 42.5, 54.4. HRMS calcd for C$_7$H$_{18}$N$_2$H: 131.1543. found 131.1549.

Example 6

Synthesis of Compound 43

2,3-Dimethoxy-N-(4-(dimethylamino)-4-methylpentyl)-8,9-methylenedioxybenzo[i]phenanthridine-12-carboxamide (43)

Compound 43 was synthesized from acid 2 using a similar procedure for 34 except the amine used was 2-dimethylamino-2-methylpentylamine (41). Light yellow solid 19 mg was obtained in 79% yield; mp 235-237° C.; IR (KBr) 1623; $^1$H NMR (CDCl$_3$) δ 1.32 (s, 6H), 1.79 (m, 4H), 2.52 (s, 6H), 3.63 (m, 2H), 3.99 (s, 3H), 4.08 (s, 3H), 6.06 (s, 2H), 7.35 (s, 1H), 7.39 (s, 1H), 7.64 (s, 1H), 7.92 (s, 1H), 8.04 (s, 1H), 9.67 (s, 1H); HRMS calcd for C$_{29}$H$_{33}$N$_3$O$_5$H: 504.2480. found 504.2478.

The required amine, 2-dimethylamino-2-methylpentylamine (41) was prepared as follows.

2-Dimethylamino-2-methylpentylamine (41)

To a solution of KCN (1.55 g, 23.8 mmol) in acetonitrile was added 18-crown-6 (229 mg, and then compound 37 (1.3 g, 8.1 mmol) was added. The reaction mixture was heated to reflux overnight and concentrated. The residue was partitioned in chloroform and water and the organic solvent was concentrated to give a yellow oil 400 mg, in 38% yield. To a suspension of LAH (380 mg, 10 mmol) in 150 mL ether was added a solution of previously obtained oil (350 mg, 2.7 mmol) in ether (2 mL) dropwise at −5° C. The reaction was stirred at room temperature for 5 hours and then cooled down to −5° C. 0.4 mL water, 0.4 mL 15% NaOH and 1.2 mL water were added sequentially. The resulting mixture was filtered and filtrate was extracted with water, brine and dried over Na$_2$SO$_4$. The organic extract was concentrated under vacuum and then distilled to afford a colorless water-like liquid 320 mg in 82% yield. $^1$H NMR (CDCl$_3$) δ 1.00 (s, 6H), 1.40 (m, 2H), 1.46 (m, 2H), 2.20 (s, 6H), 2.68 (m, 2H).

Example 7

Synthesis of Compound 44

2,3-Dimethoxy-8,9-methylenedioxybenzo[i]phenanthridine-11-carboxylic acid 3-(dimethylamino)-3-methylbutylamide (44)

Compound 44 was synthesized from acid 3 using a similar procedure for 34 except the amine used was 2-dimethylamino-2-methylbutylamine (40). Light yellow solid 17 mg was obtained in 70% yield; mp 233-235° C.; IR (KBr) 1641; $^1$H NMR (CDCl$_3$) δ 1.49 (s, 6H), 2.24 (m, 2H), 2.79 (s, 6H), 3.59 (m, 2H), 4.00 (s, 3H), 4.08 (s, 3H), 6.13 (s, 2H), 7.25 (s, 1H), 7.35 (s, 1H), 7.62 (s, 1H), 7.88 (s, 1H), 8.08 (s, 1H), 9.72 (s, 1H); HRMS calcd for C$_{28}$H$_{31}$N$_3$O$_5$H, 490.2336. found 490.2327.

Example 8

Synthesis of Compound 45

2,3-Dimethoxy-8,9-methylenedioxybenzo[i]phenanthridine-11-carboxylic acid 4-(dimethylamino)-4-methylpentylamide (45)

Compound 45 was synthesized from acid 3 using a similar procedure for 34 except the amine used was 2-dimethylamino-2-methylpentylamine (41). Light yellow solid 15 mg was obtained in 62% yield; mp 239-242° C.; IR (KBr) 1649; $^1$H NMR (CDCl$_3$) δ 1.42 (s, 6H), 1.87 (m, 4H), 2.63 (s, 6H), 3.61 (m, 2H), 4.07 (s, 3H), 4.20 (s, 3H), 6.22 (s, 2H), 7.49 (s, 1H), 7.84 (s, 1H), 8.04 (s, 1H), 8.17 (s, 1H), 8.46 (s, 1H), 9.83 (s, 1H); HRMS calcd for C$_{29}$H$_{33}$N$_3$O$_5$H, 504.2480. found 504.2481.

Example 9

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

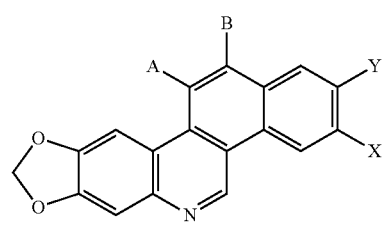

wherein:
one of A and B is —C(O)NH(CR$^6$R$^7$)$_n$CR$^1$R$^2$NR$^a$R$^b$ and the other is H;
R$^1$ and R$^2$ are each independently (C$_1$-C$_3$) alkyl;
R$^a$ is (C$_1$-C$_3$) alkyl;
R$^b$ is (C$_1$-C$_3$) alkyl;
for each CR$^6$R$^7$; R$^6$ and R$^7$ are each independently H or CH$_3$;
n is 1, 2, or 3;
X is —OCH$_3$ and Y is —OR$^3$; or Y is —OCH$_3$, and X is OR$^3$;
R$^3$ is H, CH$_3$, —C(O)R$^4$, —C(O)OR$^5$ or —C(O)NR$^c$R$^d$;
R$^4$ is (C$_1$-C$_6$)alkyl, aryl, heteroaryl, aryl(alkyl), heteroaryl(alkyl), or (C$_3$-C$_6$)cycloalkyl;
R$^5$ is (C$_1$-C$_6$)alkyl, aryl, heteroaryl, aryl(alkyl), heteroaryl(alkyl), or (C$_3$-C$_6$)cycloalkyl; and
R$^c$ and R$^d$ are each independently H, aryl, heteroaryl, aryl(alkyl), heteroaryl(alkyl), or (C$_1$-C$_6$)alkyl; or R$^c$ and R$^d$ together with the nitrogen to which they are attached form a piperazino, pyrrolidino or piperidino;
or a salt thereof.

2. The compound of claim 1 wherein A is —C(O)NH (CR$^6$R$^7$)$_n$CR$^1$R$^2$NR$^a$R$^b$ and B is H.

3. The compound of claim 1 wherein B is -C(O)NH (CR$^6$R$^7$)$_n$CR$^1$R$^2$NR$^a$R$^b$ and A is H.

4. The compound of claim 1 wherein each CR$^6$R$^7$ is CH$_2$.

5. The compound of claim 1 wherein A is —C(O)NHCH$_2$C(CH$_3$)$_2$N(CH$_3$)$_2$, —C(O)NH(CH$_2$)$_2$C(CH$_3$)$_2$N(CH$_3$)$_2$ or —C(O)NH(CH$_2$)$_3$C(CH$_3$)$_2$N(CH$_3$)$_2$.

6. The compound of claim 1 wherein B is —C(O)NHCH$_2$C(CH$_3$)$_2$N(CH$_3$)$_2$, —C(O)NH(CH$_2$)$_2$C(CH$_3$)$_2$N(CH$_3$)$_2$ or —C(O)NH(CH$_2$)$_3$C(CH$_3$)$_2$N(CH$_3$)$_2$.

7. The compound of claim 1 wherein X is —OCH$_3$ and Y is —OR$^3$.

8. The compound of claim 1 wherein Y is —OCH$_3$ and X is —OR$^3$.

9. The compound of claim 7 wherein R$^3$ is —C(O)R$^4$, —C(O)OR$^5$ or —C(O)NR$^c$R$^d$.

10. The compound of claim 9 wherein R$^4$ and R$^5$ are (C$_1$-C$_6$)alkyl.

11. The compound of claim 9 wherein R$^c$ and R$^d$ are each independently H or (C$_1$-C$_6$)alkyl.

12. The compound of claim 7 wherein $R^3$ is $CH_3$.

13. The compound 2,3-dimethoxy-N-(2-(dimethylamino)-2-methylpropyl)-8,9-methylenedioxybenzo[i]phenanthridine-12-carboxamide;
- or 2,3-dimethoxy-8,9-methylenedioxybenzo[i]phenanthridine-11-carboxylic acid 2-(dimethylamino)-2-methylpropylamide;
- or 2,3-dimethoxy-N-(3-(dimethylamino)-3-methylbutyl)-8,9-methylenedioxybenzo[i]phenanthridine-12-carboxamide;
- or 2,3-dimethoxy-N-(4-(dimethylamino)-3-methylpentyl)-8,9-methylenedioxybenzo[i]phenanthridine-12-carboxamide;
- or 2,3-dimethoxy-8,9-methylenedioxybenzo[i]phenanthridine-11-carboxylic acid 3-(dimethylamino)-3-methylbutylamide; or
- 2,3-dimethoxy-8,9-methylenedioxybenzo[i]phenanthridine-11-carboxylic acid 4-(dimethylamino)-4-methylpentylamide or a salt thereof.

14. A composition comprising a compound of formula I as described in claim 1, or a pharmaceutically acceptable salt thereof, and a pharmaceutically acceptable excipient, diluent or carrier.

15. The compound of claim 1 wherein n is 1.

16. The compound 2,3-dimethoxy-N-(2-(dimethylamino)-2-methylpropyl)-8,9-methylenedioxybenzo[i]phenanthridine-12-carboxamide or a salt thereof.

17. The compound 2,3-dimethoxy-8,9-methylenedioxybenzo[i]phenanthridine-11-carboxylic acid 2-(dimethylamino)-2-methylpropylamide or a salt thereof.

* * * * *